United States Patent [19]

Dougherty

[11] Patent Number: 4,471,890
[45] Date of Patent: Sep. 18, 1984

[54] EYE DROP DISPENSER

[75] Inventor: Delford O. Dougherty, Cleveland, Ohio

[73] Assignee: St. Luke's Hospital, Cleveland, Ohio

[21] Appl. No.: 372,966

[22] Filed: Apr. 29, 1982

[51] Int. Cl.³ .............................................. A61M 31/00
[52] U.S. Cl. ................................... 222/190; 222/420; 604/302
[58] Field of Search ................... 222/420, 190; 401/6, 401/48, 193; 604/300, 302

[56] References Cited

U.S. PATENT DOCUMENTS

| 3,058,466 | 10/1962 | Routsong . | |
| 3,279,466 | 10/1966 | Mings . | |
| 3,521,636 | 7/1970 | Mahoney et al. . | |
| 3,722,216 | 11/1955 | Robbins . | |
| 3,872,866 | 3/1975 | Lelicoff | 604/302 |
| 3,934,590 | 1/1976 | Campagna . | |
| 4,002,168 | 1/1977 | Petterson | 604/302 X |
| 4,392,590 | 7/1983 | Hofmann-Igl | 222/174 |

FOREIGN PATENT DOCUMENTS

| 502432 | 4/1951 | Belgium | 222/420 |
| 29147 | 5/1981 | European Pat. Off. . | |
| 170777 | 3/1960 | Sweden | 222/420 |

Primary Examiner—H. Grant Skaggs
Assistant Examiner—Frederick R. Handren
Attorney, Agent, or Firm—Body, Vickers & Daniels

[57] ABSTRACT

An eyedrop dispenser for dispensing droplets of liquid from a container comprises a closure cap member for liquid tight attachment to the container. At least one projection extends laterally outward from the cap member and has a laterally outward facing surface for bracing against a portion of the head of a person to locate and steady the dispenser during use.

2 Claims, 5 Drawing Figures

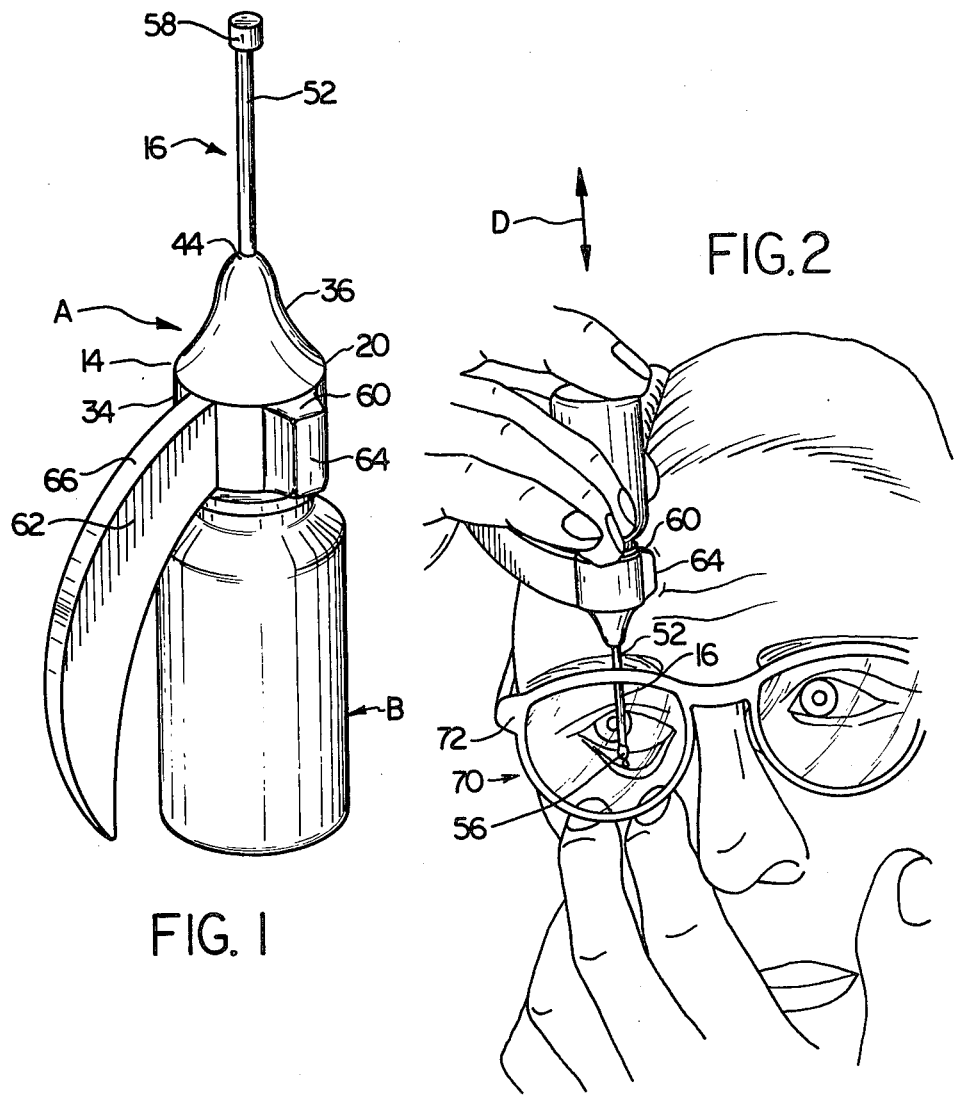

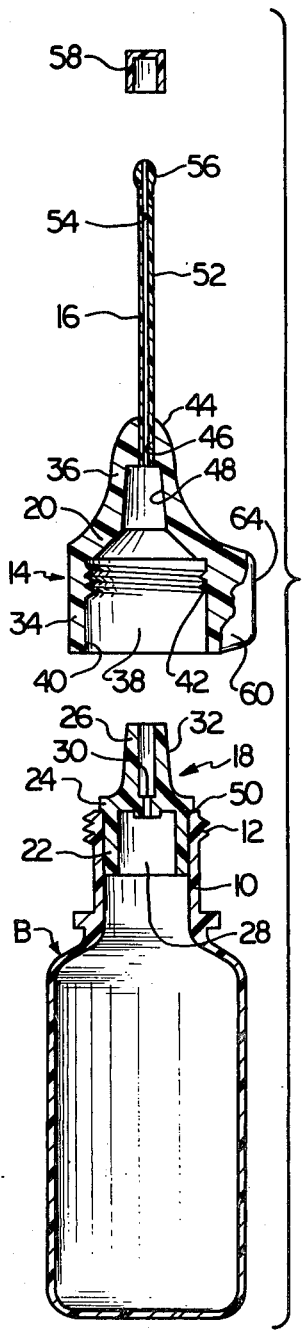
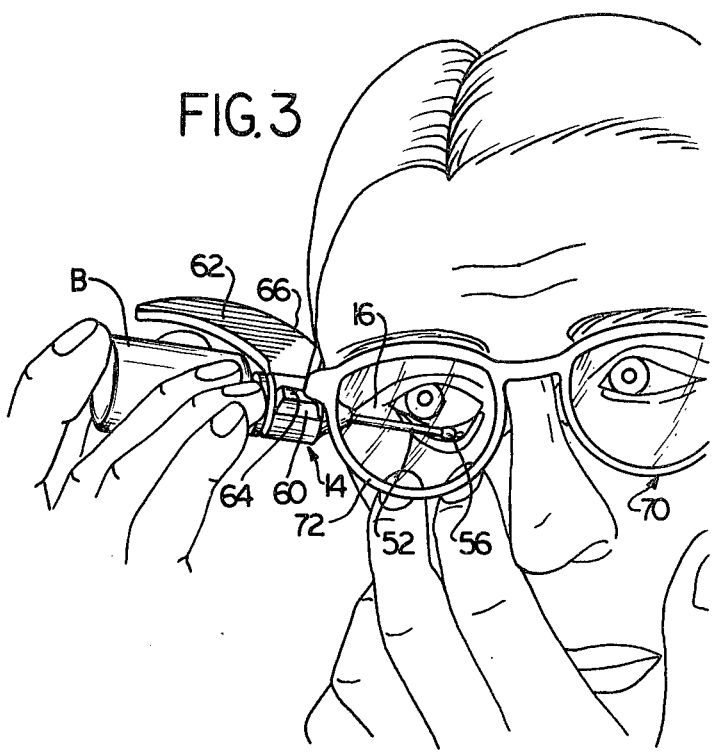
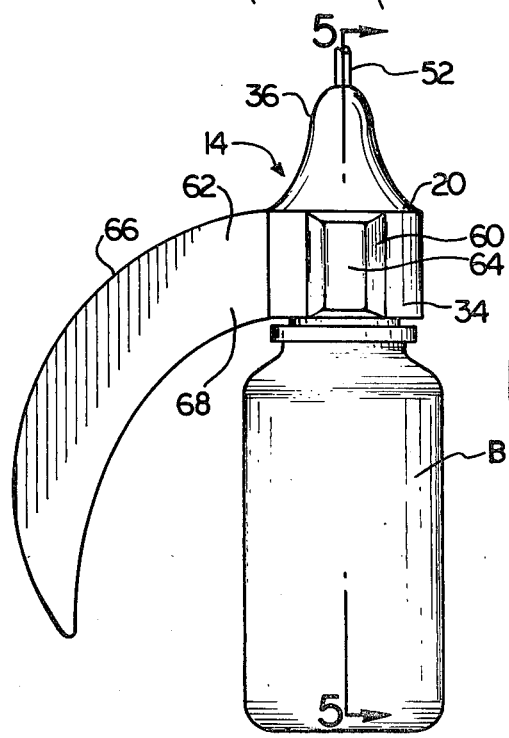

EYE DROP DISPENSER

BACKGROUND

The present invention pertains to the art of liquid dispensers, and more particularly to a manually held drop dispenser for accurately and easily dispensing small amounts of liquids at confined drop-releasing locations. The present invention is particularly applicable to an eye drop dispenser and will be described with reference thereto.

BACKGROUND OF THE INVENTION

Eye drop dispensers of the type to which this invention pertains are available in various sizes and shapes for the numerous medicines and solutions which are available for the care and comfort of the human eye and which are in most cases very expensive. Heretofore, such dispensers basically comprised a relatively small compressible plastic container or vial provided with a drop dispensing cap. The cap is generally provided with a dispensing nozzle having a small drop-dispensing orifice or opening therein at its outer end.

One of the special problems associated with these prior drop dispensers is the proper positioning and controlling of the dispensing nozzle when inserting medicant drops into the human eye. Accurate placement of the drops is very important. Most medicants for the human eye are extremely expensive; a single drop can cost upward of several dollars each. The loss or waste of even a few drops therefore can represent a substantial expense. The insertion of these drops generally requires the rigid nozzle of the dispenser to be positioned or located near the surface of the eye. A steady hand and firm control of the dispenser is required to accurately hold it steady in space in order to properly direct the medicant drops into the eye and prevent waste of expensive medicant, and more importantly, to avoid possible injury to the eye by accidental contact of the rigid nozzle end with the delicate surface of the eye. But with the rigid nozzle end of the manually held dispenser positioned in such close proximity to the eye, it becomes difficult to visually focus on the nozzle end and, as a result, eye-hand coordination is generally impaired. In addition, the hand and arm of the person applying the drops are held in an outward unbraced position in space which thus further impairs an individual's ability to steady or control the position of the dispenser in space relative to the eye. This problem is compounded for people in advanced years and failing eyesight who are not capable of holding their hand steady in such an outward position in space and are unable to focus on an object so near the surface of the eye.

THE INVENTION

The present invention contemplates a new and improved dispenser device for dispensing droplets of liquid which overcomes all of the above-referred to difficulties and others, and provides a liquid medicant dispenser with means to steady and control the position of the dispenser when manually held near the surface of the eye, which accurately dispenses droplets of liquid medicine at desired locations without waste of expensive medicants, and which is simple, accurate, economical and easy to use.

In accordance with one aspect of the present invention, a dispensing device comprising a cap member for liquid-tight attachment to a container from which liquid droplets such as eye drops are to be dispensed and having a nozzle extending endwise from the container and formed with a drop dispensing outer tip end, is provided with at least one locating projection extending laterally outward from the cap member and provided with a laterally outward facing rest surface located in predetermined spacial relation to the nozzle tip end. The rest surface acts as a pivoting brace point, when positioned against a portion of the head of an individual, to enable accurate locating and steady control of the position of the nozzle end of the dispenser in relationship to the eye.

In accordance with a further aspect of the invention, the aforementioned rest surface may be formed either by a convex laterally outward facing surface on an arm extending laterally outward from the side of the cap member and generally alongside the container, or by a laterally outward facing generally flat surface formed on the locating projection and disposed generally parallel to the axis of the nozzle.

In accordance with a still further aspect of the invention, the nozzle portion of the cap member is provided with an elongated dispensing tube extending endwise therefrom and terminating in a tip end from which the liquid droplets are dispensed. The dispensing tube may comprise a somewhat flexible type plastic tube of sufficiently small cross-sectional size and sufficient length to enable insertion thereof in the restricted space between a person's eye and any corrective eyeglasses which the person may be wearing.

OBJECTS

The principal object of the invention is the provision of a new and improved device for dispensing drops of liquid medicant which is simple and economical in construction and easy to use, and will prevent waste of medicant.

Another object of the invention is the provision of an eye drop dispenser which enables the dispensing tip thereof to be easily located and held in steady, controlled drop dispensing position near the surface of the eye.

A further object of the present invention is the provision of an eye drop dispenser having rest surfaces thereon whereby the dispenser can be held against a portion of the head of an individual to locate and steady the dispensing tip end of the dispenser with relation to the eye.

DRAWINGS

The invention may take physical form in certain parts and arrangement of parts, the preferred embodiment of which is described in detail in the specification and illustrated in the accompanying drawings wherein:

FIG. 1 is a perspective view of a liquid medicant dispenser assembly equipped with a drop dispenser device comprising the invention;

FIG. 2 is a view showing one manner of use of the drop dispenser assembly shown in FIG. 1;

FIG. 3 is a view showing a second manner of use of the drop dispenser assembly;

FIG. 4 is a side elevation view of the medicant dispenser assembly shown in FIG. 1; and, FIG. 5 is an expanded sectional view of the dispenser assembly taken along the lines 5—5 of FIG. 4.

PREFERRED EMBODIMENT

Referring now to the drawings wherein the showings are for the purpose of illustrating a preferred embodiment of the invention only and not for the purpose of limiting same, FIG. 1 shows an assembly of a liquid drop dispensing device A comprising the invention with a compressible plastic container or vial B containing a supply of liquid medicant to be dispensed in droplet form, such as eye drops for instance. Container B forms no part of the present invention and is shown relatively conventionally. Normally, any plastic container or vial B such as commonly used in conjunction with an eye drop dispenser would include a reduced diameter open neck portion 10 provided with external helical screw threads 12 over the uppermost part of the neck end portion as shown in FIG. 5. The screw threads 12 are adapted to matingly engage internal threads on dispensing device A to thereby attach the latter in place on the container B in liquid-tight relation thereto. Device A is comprised of a closure assembly 14 and, in the particular case shown, also an elongated dispensing member 16.

As shown in FIG. 5, the closure assembly 14 is comprised of an insert or stopper 18 and a cap member 20 both of which may be made of a suitable plastic material. The insert 18 is of a standard type such as employed in eye drop dispensers commonly in use at present and comprises, in general, a cylindrical inner stopper portion 22 adapted to snugly fit substantially liquid-tight into the opening in the neck end 10 of the container B, an intermediate annular collar portion 24, and a cap-engaging outer portion 26. The insert 18 is provided with an axial passageway 28 therethrough having a short constricted section 30 for restricting the flow of the liquid medicant from the container B through the passageway 28 on manual compressing of the container. The cap-engaging outer portion 26 of the insert 18 is of circular cross-section with its exterior surface slightly tapered down in diameter toward its outer end to form a frusto-conical exterior surface 32.

The cap member 20 comprises a generally cylindrical mounting or base portion 34 and a nozzle end portion 36 projecting endwise therefrom. An axial passageway 38 of varying diameter extends centrally through the cap member. The portion 40 of the passageway which extends through the base portion 34 of the cap member 20 is of a diameter to fit over, and is provided with helical screw threads 42 for mating engagement with the external screw threads 12 on the neck end portion 10 of the container B to attach the cap member thereto. The nozzle end portion 36 of the cap member 20 is of generally conical exterior shape tapering down in diameter from the base portion 34 of the cap member to an outer apex or tip end 44. Within the nozzle end portion 36 of the cap member 20, the axial passageway 38 therethrough decreases in diameter from the threaded portion 40 thereof toward the apex end 44 of the cap member to a relatively small diameter bore opening 46 within the apex end 44 of the nozzle end portion 36. Midway through the axial extent of the nozzle end portion 36 of the cap member 20, the internal passageway 38 thereof is formed with a frusto-conical shaped section 48 of slightly tapered form corresponding to the frusto-conical exterior surface 32 of the insert 18 for wedging engagment therewith when the cap member 20 is screwed onto the threads 12 of the container neck end 10. This wedging action forces the insert 18 inwardly into the container neck end until the annular collar 24 of the insert abuts against the rim 50 of the container neck end 10 to form a liquid-tight seal therebetween.

The structure of the dispensing device A as so far described is of conventional form such as employed in eye drop dispensers commonly in use at present, and forms no part of the present invention.

In the preferred embodiment of the invention, the closure assembly 14 is provided with the aforementioned elongated dispensing member 16 on the nozzle end portion 36. This member 16 is preferably comprised of a small diameter, e.g., around 1/16 inch or so, somewhat flexible tube 52 formed of a suitable plastic material and having an internal passageway or bore 54 extending axially therethrough. One end of the dispensing tube 52 is force fitted into or otherwise suitably secured in the bore opening 46 of the cap member 20 to firmly secure the dispensing tube in place on the cap member in endwise extending and fluid-tight relation thereto. The dispensing tube 52 is preferably provided with a rounded outer end 56 to afford a protective, smooth-surfaced, droplet dispensing tip end from which droplets of liquid medicant are expelled when the container B is manually compressed or squeezed. A protective cover or closure cap 58 suitably made of a plastic material is provided to fit tightly over and seal off the dispensing tip end 56 of the tube 52 when the droplet dispenser assembly is not in use.

In accordance with the invention, the cap member 20 is provided with locating means for resting against a portion of the head of a person to enable accurate locating and steady holding of the tip end 56 of the dispensing tube 52 in the desired proper droplet-dispensing use position relative to the person's eye. The locating means comprises one or more laterally outward extending projections, such as the projection 60 and/or the projection 62 (FIGS. 1 and 4) molded on or otherwise integrated with the cylindrical mounting or base portion 34 of the cap member 20, which projections 60, 62 are provided with respective rest surfaces 64 and 66, located in predetermined spacial relation to the dispenser tube tip end 56, for resting against a person's head. As shown, the projections 60, 62 are suitably spaced apart around the circumferential extent of the cap member, for instance, angularly spaced at least around 45° or so apart about the central axis of the cap member.

The locating projection 60 is in the form of a raised pad or mound of rectangular or similar configuration, on the exterior surface of the cylindrical base portion 34 of the cap member 20. The laterally outward facing rest or top surface 64 of locating projection 60 may, as shown, be in the form of a flat planar surface disposed generally in a plane parallel to the axis of the cap member 20 and normal to that radial plane thereof which bisects the projection 60. If desired, the rest surface 64 may be of somewhat rounded form in either or both its longitudinal and/or lateral directions.

The locating projection 62 is in the form of an arm extending laterally outward from the exterior surface of the base portion 34 of cap member 20 and downwardly away from the nozzle end 36 thereof and alongside the container B. The rest surface 66 of the arm-shaped projection 62 is of convexly arcuate form with the portion thereof nearest the cap member 20 facing in the direction of the nozzle end 36 thereof and the remaining or outward portion thereof facing generally laterally outward of the container B. In effect, the arcuate-shaped rest surface 66 may have a center of curvature located more or less adjacent the extended axis of the closure assembly 14 at a point spaced from the cap member 20 thereof in a direction opposite to the direction in which the dispenser tube 52 projects from the cap member. In its preferred form as shown principally in FIGS. 1 and 4, the arm-like projection 62 is of truncated lune shape configuration with its truncated end 68 adjoining the cylindrical base portion 34 of the cap member 20. It should be understood, however, that the arm-like projection 62 may be of any suitable configuration so long as it is provided with a rest surface 66 of the convex outward shape and facing in the direction as described above and located in predetermined spacial relation to the tip end 56 of the dispenser tube 52.

FIGS. 2 and 3 show two methods of using the droplet dispenser device comprising the present invention. Both figures show, and will be described with reference to an individual wearing eyeglasses 70. It will be appreciated however, that the invention is applicable to, and equally useful for individuals not wearing eyeglasses.

FIG. 2 shows a method of inserting eye drops from above the eye. Rest surface 64 on projection 60 is positioned against the individual's forehead above the eye. Using surface 60 to stabilize and control the position of the dispenser, tip end 56 of the dispenser tube 52 can be positioned between the frames 72 of the eyeglasses 70 and the surface of the eye. The dispensing tip end 56 can be located near the lower eyelid at the proper dispensing position by guiding the dispenser assembly, with its locating surface 64 resting on the individual's forehead, up and down along the forehead in a direction shown by arrow D in FIG. 2. When tip end 56 is in proper vertical dispensing position relative to the eye, rest surface 64 then can be used as a sort of rocker surface to enable pivoting of the dispensing tip inwardly near the eye. By thus using the forehead as a stabilizing surface, the dispensing tip 56 can be brought relatively close to the surface of the eye under firm and steady control without the fear of accidental contact with the eye. In addition, because of its narrow tubular construction, the dispensing member 16 does not obstruct the individual's version when using a mirror to locate the dispensing tip. Also, because dispensing member 16 can be inserted between the surface of the eye and the eyeglasses 70, individuals with poor eyesight can obtain the visual benefits provided by their eyeglasses and therefore can use a mirror to accurately position the dispensing tip 56 in proper dispensing position near the eye.

In a similar manner, FIG. 3 shows a method of inserting eye drops from the side of an individual's eye. Because of the curvature of the temple region on the side of an individual's head, the locating arm member 62 is provided with the arcuate shaped rest surface 66. When held against the side of the individual's head, rest surface 66 provides, in a manner similar to that provided by the rest surface 64 as described above, a rocker type surface for pivotally adjusting the position of the dispensing tip 56 relative to the eye. The narrow dispensing member 16 does not interfere with the individual's vision and can be used even while the individual is wearing eyeglasses 70.

From the above description, it will be evident that the present invention provides a drop dispenser for applying eye drops which affords two different easy and accurately controllable methods of safely inserting eye drops without loss of expensive medicant and either of which can be carried out while eyeglasses remain in place. Also, while in the preferred embodiment of the invention the dispenser device A is provided with an elongated dispenser member or tube 16 on the nozzle end portion 36, such an elongated dispenser member may be omitted and the nozzle tip end 44 of the cap member 20 employed instead to dispense the droplets from the container B. In such case, the locating surfaces 64 or 66 are used in the same manner as described hereinabove for accurately locating the nozzle end 44 of the dispensing device A in proper droplet dispensing position relative to the individual's eye.

It will be appreciated that other embodiments of the present invention exist and that other additional modifications and alterations will occur to others upon a reading and understanding of this specification. It is intended that all such modifications and alterations be included insofar as they come within the scope of the appended claims or the equivalents thereof.

Having thus described the invention, the following is claimed:

1. A device for dispensing droplets of a liquid from a container having an open neck end, said device comprising a closure cap member for liquid-tight attachment to the neck end of the container, an outwardly projecting generally elongated, straight tubular member of small diameter extending along an axis endwise from the cap member and terminating in an outer tip end, said tubular member having an inner passageway communicating said tip end with the interior of the container, and at least one projection integrally formed with and extending outwardly from said cap member having a laterally outward facing rest surface thereon, said projection extending from its point of attachment to said cap member laterally outwardly and away from said tip end in a direction parallel to said axis, whereby said surface is located in predetermined spacial relation from said tip end of said tubular member, said rest surface being of generally arcuate shaped form with its center of curvature located adjacent said axis at a point spaced from said cap member in a direction opposite to the direction in which said tubular member extends from said cap member, whereby said surface can be braced against a portion of the head of a person such that accurate locating and steady holding of the tip end of the dispensing nozzle in a desired proper droplet dispensing use position can be attained.

2. A device for dispensing droplets of a liquid from a container having an open neck end, said device comprising a closure cap member for liquid-tight attachment to the neck end of the container, an outwardly projecting elongated, generally straight tubular dispenser member of small diameter extending along an axis endwise from the cap member and terminating in an outer tip end, said member having an inner passageway communicating said tip end with the interior of the container, and two projections integrally formed with and extending outwardly from said cap member, each having a laterally outward facing rest surface thereon, said projections displaced from said dispensing tip along said axis and extending generally laterally outwardly from said axis, whereby said surfaces are located in predetermined spacial relation to the tip end of said dispenser member, one of said projections having a laterally outward facing generally flat planar surface disposed in a plane generally parallel to the axis of said dispenser member, and the other of said projections extending from its point of attachment to said cap member laterally outwardly and away from said tip end in a direction parallel to said axis, said other of said projections having a rest surface of generally arcuate shaped form facing in a direction laterally outward of said cap member and with its center of curvature located adjacent said axis of said dispenser member at a point spaced from said cap member in a direction opposite to the direction in which the said dispenser member projects from said cap member, whereby each of said surfaces can be individually braced against a portion of the head of a person such that accurate locating and steady holding of the tip end of the dispensing nozzle in a desired proper droplet dispensing use position can be attained.

* * * * *